United States Patent [19]

Nieusma, Jr.

[11] Patent Number: 4,880,381

[45] Date of Patent: Nov. 14, 1989

[54] BARRIERS FOR DENTAL AND MEDICAL HANDPIECE HANGERS

[76] Inventor: Dick H. Nieusma, Jr., 13658 Hanford Ct., Warren, Mich. 48093

[21] Appl. No.: 218,973

[22] Filed: Jul. 14, 1988

[51] Int. Cl.$^4$ .............................................. A61C 1/02
[52] U.S. Cl. ...................................... 433/28; 433/106
[58] Field of Search .................... 433/28, 29, 114, 116, 433/77

[56] References Cited

U.S. PATENT DOCUMENTS 4,806,099  2/1989  Peralta ................................. 433/28
4,810,194  3/1989  Snedden ............................... 433/28

Primary Examiner—Robert Peshock
Attorney, Agent, or Firm—Price, Heneveld, Cooper, DeWitt & Litton

[57] ABSTRACT

A draping apparatus for covering dental and medical handpiece hangers. The apparatus is made from thin aluminum foil or from an aluminum foil-plastic film laminate. It is molded to allow rapid and convenient placement into handpiece hangers and the "dead soft" aluminum foil allows accurate adaptation of the cover to the hanger by finger pressure. A modification of the barrier includes a rectangular window where the aluminum is removed, exposing the translucent plastic film and allowing the function of auto-handpiece selector switches, either mechanical or photoelectric.

19 Claims, 4 Drawing Sheets

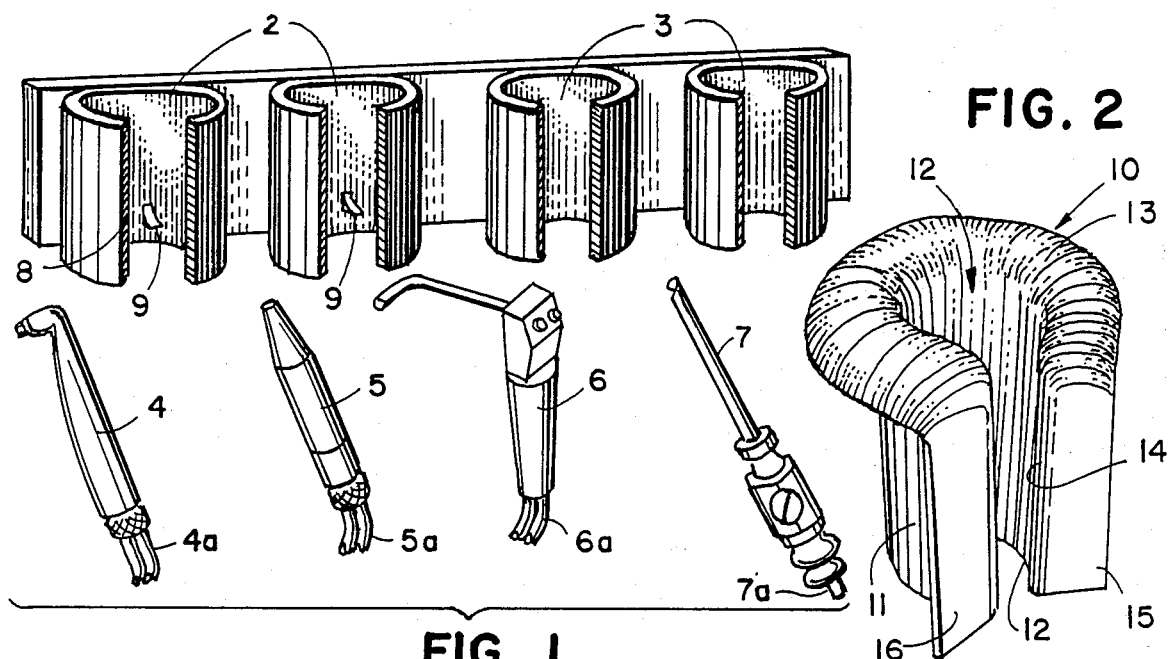
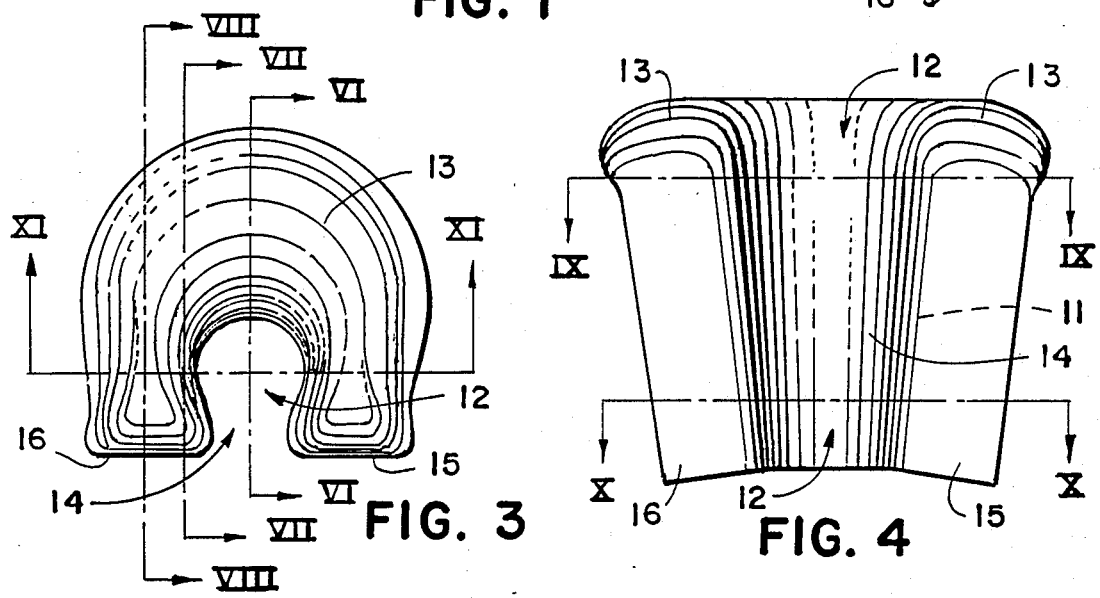
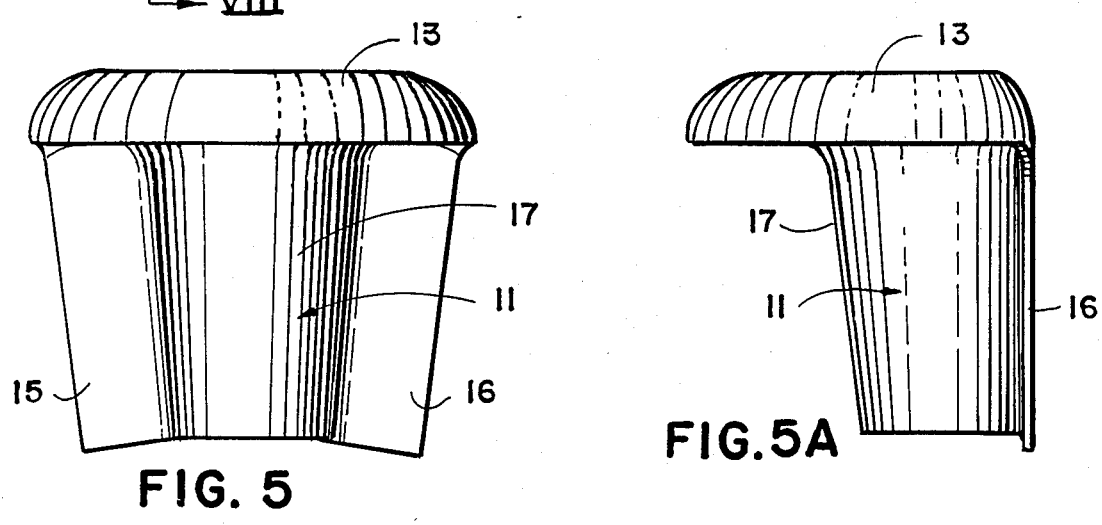

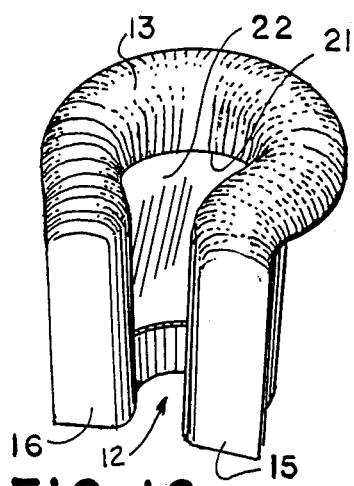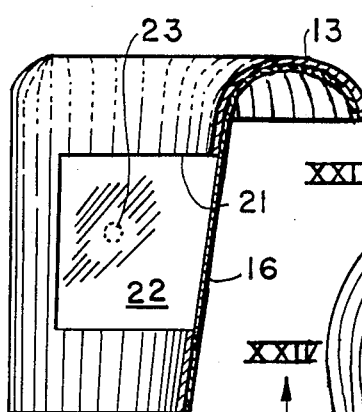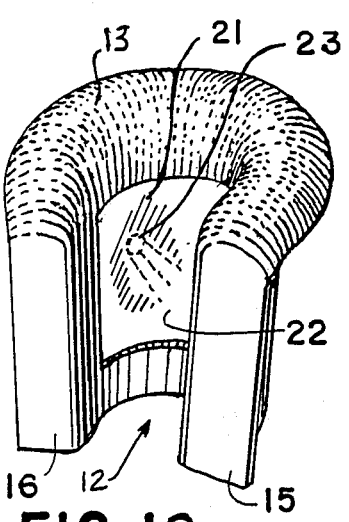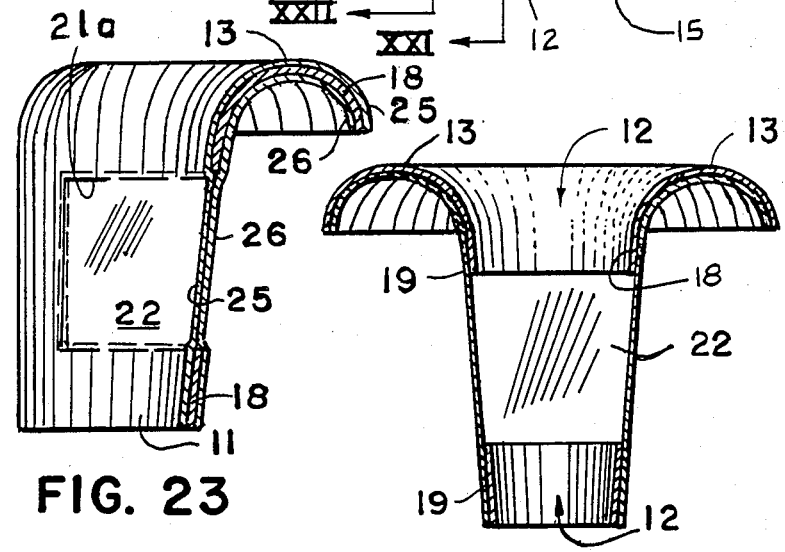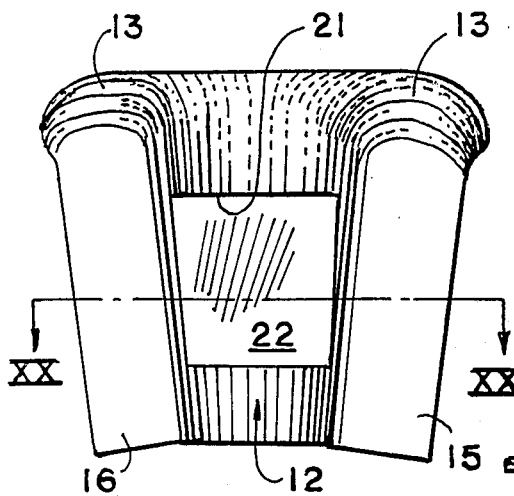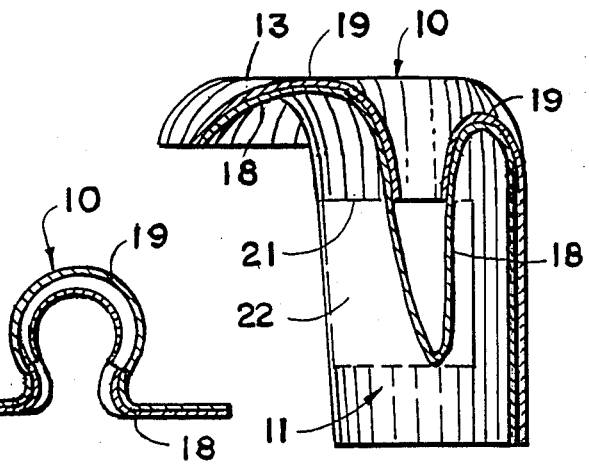

BARRIERS FOR DENTAL AND MEDICAL HANDPIECE HANGERS

This invention relates to a device for preventing or at least minimizing the transmission of infectious micro-organisms when placing dental and medical handpieces in their hangers during treatment

BACKGROUND OF THE INVENTION

Dental and medical handpieces become contaminated with micro-organisms during treatment, and when these handpieces are placed into their hangers this contamination is transmitted to the hangers. If this contamination is not prevented or eliminated, there is a danger of transmission to the next patient of organisms remaining on these hangers.

One method of addressing this problem is spraying and scrubbing with disinfectant and then waiting about 10 minutes for the disinfectant to take effect. There is no way to completely sterilize these hangers in the equipment in common use at present. Another method is to cover the hangers, either with a garment-type plastic bag over the instrument tray and all of the hangers, or to wrap clinging plastic film or aluminum foil over each hanger. Because of the time required, the lack of convenience and effectiveness of these present methods, there has been a need for some way to assure or at least minimize the transmission of infectious micro-organisms when placing and removing dental and medical handpieces on and from their hangers.

Other drapes known by me for covering dental or medical equipment are disclosed in U.S. Pat. Nos. 1,093,865, 1,342,968, 1,485,963, 1,539,253, 1,682,784, 3,528,720, 3,698,791 and my own U.S. Pat. No. 4,723,912. In these devices, tubular or sack-like envelopes of latex, hard paper or synthetic plastic films are used to slip over and enclose dental handpieces, operating microscopes and their appendages. All of these devices are not suitable for solving the problem of preventing transmission of infectious micro-organisms from instrument hangers.

SUMMARY OF THE INVENTION

This invention accomplishes the desired result and solves a long felt need by providing a preformed, disposable, sanitary barrier that is inexpensive, can easily be installed without contaminating the hands or the equipment, can be sterilized, stays in place well while removing and replacing the handpiece from the hanger, and can be quickly removed and replaced by a sanitary barrier after treatment is complete.

The barrier of the present invention is a molded shell of thin (approximately 0.001"), deformable, aluminum foil which has essentially no memory and can easily and quickly be slipped into any handpiece hanger, adapted to the inside of the hanger by placement of the handpiece, and then adapted to the outside of the hanger by finger pressure while the handpiece is in place in the hanger. Removing the handpiece and completing the adaptation with finger pressure locks the barrier firmly on the hanger.

Because the aluminum foil is deformable and essentially has no memory, it can be made to conform to the shape of the hanger where it stays in place while the handpiece is repeatedly removed and replaced in the hanger. Being made of metallic aluminum, the invention can be sterilized under steam for use in aseptic surgical conditions.

In another embodiment of this invention, the aluminum foil is bonded as a laminate with a thin, tough, plastic film. The aluminum foil permits in-place, custom molding of the barrier to the hanger, and the plastic film adds toughness to prevent perforation or tearing of the aluminum foil during treatment procedures.

In still another embodiment of this invention, a rectangular portion of the aluminum foil is removed from the center of where it contacts the inside of the hanger, and the opening in the aluminum foil exposes the laminated plastic film in that area. The purpose of this plastic "window" is to permit the use of the invention with certain hangers with automatic handpiece selector switches. There are two types of automatic switching hangers that might be interfered with by the use of a barrier made entirely of aluminum foil. One type contains a lever or button which is depressed when the handpiece is placed in the hanger, turning off the power to that handpiece, and which is released and activated when the handpiece is removed from the hanger. The use of the relatively inflexible aluminum foil barrier might prevent the activation of the switch, but the plastic film "window" is thin and flexible and allows the release and activation of the switch to turn power on and off as the handpiece is removed and replaced in the hanger.

Another type of hanger with automatic handpiece selector switching is based on a photo-electric switch, utilizing a beam of light and a photo-sensitive switch which turns on the power when the handpiece is removed from the hanger. When the handpiece is replaced in the hanger, the beam of light is interrupted deactivating the switch to turn off the power. A barrier of solid aluminum would block the light beam and prevent the turning on of the power to the handpiece. The translucent, plastic film insert allows normal function of the photoelectric handpiece selector switch when the handpiece is removed and replaced in the hanger.

The barrier is designed in a tapered sleeve form to allow easy removal of the barrier from the mold during manufacture, to allow insertion into hangers of various designs. The tapered shape also allows stacking of many units in a dense configuration to save space for storage or packaging and to allow removal of one unit at a time without contaminating the others.

BRIEF DESCRIPTION OF THE DRAWINGS

FIG. 1 is an elevational, perspective view of a typical handpiece hanger assembly, with the handpieces to be hung shown underneath the hangers;

FIG. 2 is a front to side-elevational, perspective view of one embodiment of the invention;

FIG. 3 is a top plan view of the FIG. 2 embodiment of the invention;

FIG. 4 is a front-elevational view of the embodiment of FIG. 2;

FIG. 5 is a rear-elevational view of the embodiment of FIG. 2;

FIG. 5A is a side-elevational view of the embodiment of FIG. 2;

FIG. 16 is a front-elevational, perspective view of another embodiment of the barrier in which the aluminum foil and plastic film laminate is utilized and a "window" of aluminum foil has been removed, exposing the thin, flexible, translucent, plastic film;

FIG. 17 is a plan view of the barrier embodiment of FIG. 16;

FIG. 18 is a side-elevational, perspective view of the embodiment of FIG. 16 illustrating the placement of the invention in a handpiece hanger containing a photoelectric handpiece selector switching mechanism;

FIG. 19 is a front-elevational view of the barrier embodiment of FIGS. 16 and 17;

FIG. 20 is a cross-sectional view taken along the plane XX—XX of FIG. 19;

FIG. 21 is a cross-sectional, elevational view taken along the plane XXI—XXI of FIG. 17;

FIG. 22 is a cross-sectional, elevational view taken along the plane XXII—XXII of FIG. 17;

FIG. 23 is a cross-sectional view like FIG. 21 illustrating an embodiment in which aluminum foil is laminated with two sheets of plastic film, one on each side, and in which a window is cut out, exposing the plastic film; and FIG. 24 is a cross-sectional view taken along the plane XXIV—XXIV of FIG. 17.

DESCRIPTION OF THE PREFERRED EMBODIMENT

Figure 6:
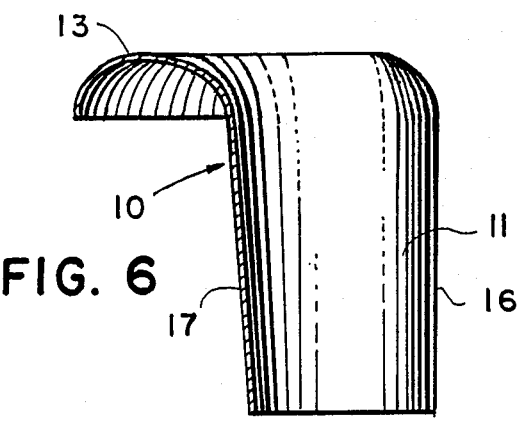
FIG. 6 is a side-elevational, cross-sectional view of the barrier of FIGS. 2–5A taken along the plane VI—VI of FIG. 3.
Figure 7:
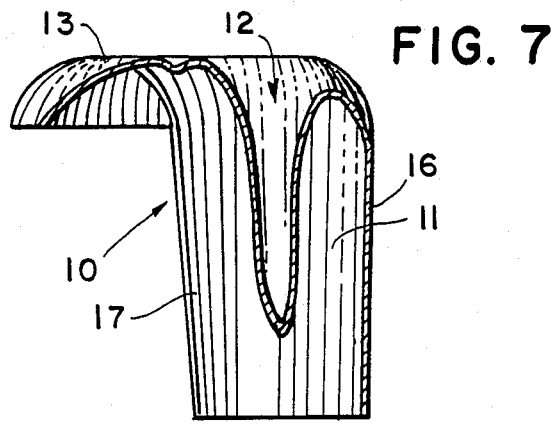
FIG. 7 is a cross-sectional, elevational view of the barrier of FIGS. 2–6 taken along the plane VII—VII of FIG. 3.
Figure 8:
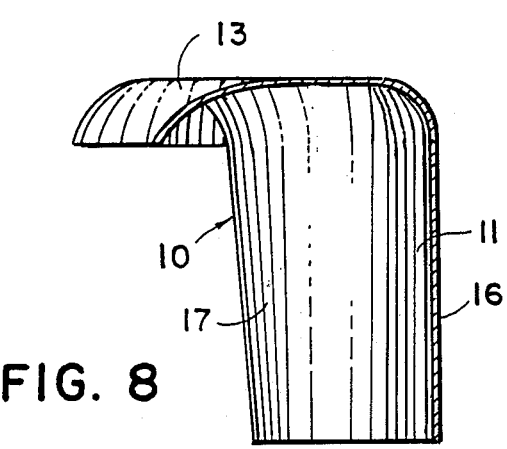
FIG. 8 is a cross-sectional, elevational view of the barrier of FIGS. 2-7 taken along the plane VIII—VIII of FIG. 3.
Figure 9:
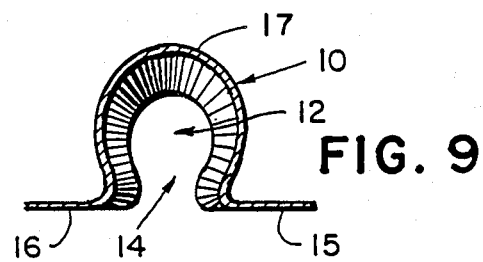
FIG. 9 is a cross-sectional, plan view of the barrier of FIGS. 2-8 taken along the plane IX—IX of FIG. 4.
Figure 10:
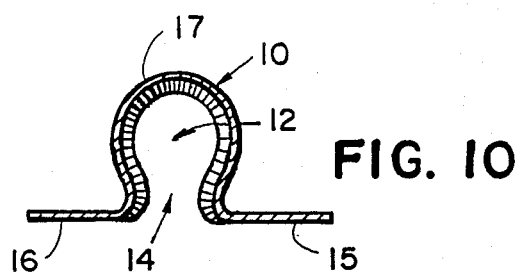
FIG. 10 is a cross-sectional, plan view of the barrier of FIGS. 2-9 taken along the plane X—X of FIG. 4.

Referring to the drawings, FIG. 1 illustrates typical handpiece hangers 2 and 3 utilized to hang various types of dental hand pieces identified by the reference numerals 4, 5, 6 and 7. The hangers 2 are of the type that contain levers 9 extending through the wall of the hangers 2 and which form part of microswitches or air valves which control the activation of the electrical or air power to the handpieces 4 and 5 when each are removed from their hangers 2. The two hangers 3 are standard, non-switching hangers commonly used for the air-water syringe instrument 6 or suction hose instrument 7. The problem that has existed is that the outsides and insides of these hangers are contaminated during dental treatment by contact of the handpiece with the operator's hand coated with blood or saliva or by fallout from air-borne debris. The present invention is provided to eliminate the transmission of such contamination from one patient to the next by providing a preformed, disposable, sanitary barrier 10 that is inexpensive, can be sterilized, and will prevent the spread of micro-organisms from one patient to the other.

Referring to FIGS. 2-14, the reference numeral 10 designates the overall disposable barrier constructed of approximately 0.001" thick aluminum foil that is preformed but deformable so that it will fit snugly within the hanger and will be retained therein despite removal and replacement of the instruments into and out of the hanger as the dentist or doctor utilizes the instruments. After the dentist or doctor completes operating on the patient, the barrier 10 is removed and replaced by another, all as will be described hereinafter.

The barrier 10 as disclosed in FIGS. 2-11 discloses an upright sleeve portion 11 having a central opening 12 which preferably is tapered from top to bottom for the purpose of more easily fitting into the quasi-cylindrical shaped holders 2 and 3. Integral with the top of the sleeve 11 is an apron 13. The sleeve 11 has a vertical opening 14 provided for the purpose of receiving the electrical or air leads, such as those identified by the reference numerals 4a, 5a, 6a and 7a (FIG. 1), when the instrument is placed into or removed from the hangers 2 or 3. Extending from this opening or slot 14 and formed integrally with the sleeve 11 are wing-like flanges 15 and 16.

The tapered form of the sleeve portion 11 allows stacking of many pieces (FIG. 12) to make a dense, confined package for storage purposes. This stacking is also designed so that the barriers can be dispensed with the back surface 17 facing outwardly to minimize touching by the operator of the front surface or barriers other than the one being dispensed. The barrier being constructed of aluminum can be sterilized in a steam autoclave.

Another embodiment of the barrier can be made of an aluminum foil and plastic film of laminated construction. In this embodiment, as disclosed in FIG. 11A, the aluminum foil-plastic film laminate comprises the aluminum laminate 18 and the plastic laminate 19. The plastic laminate 19 is a thin plastic film of approximately 0.001" thickness constructed of a material such as polyethylene.

Figure 13:
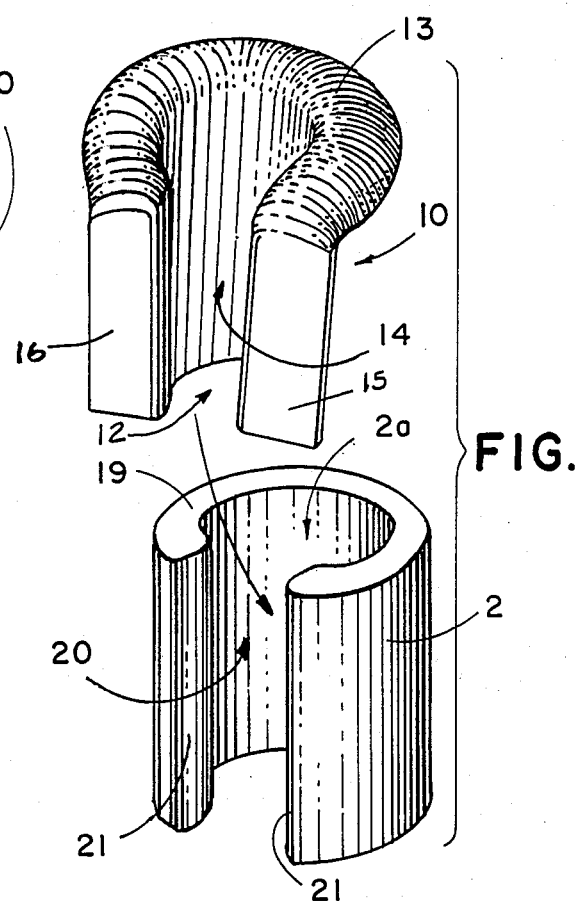
FIG. 13 is a side-elevational, perspective view of the barrier of FIGS. 2-11 illustrating the initiation of the placement of the barrier of FIGS. 2-12 in a handpiece hanger.
Figure 14:
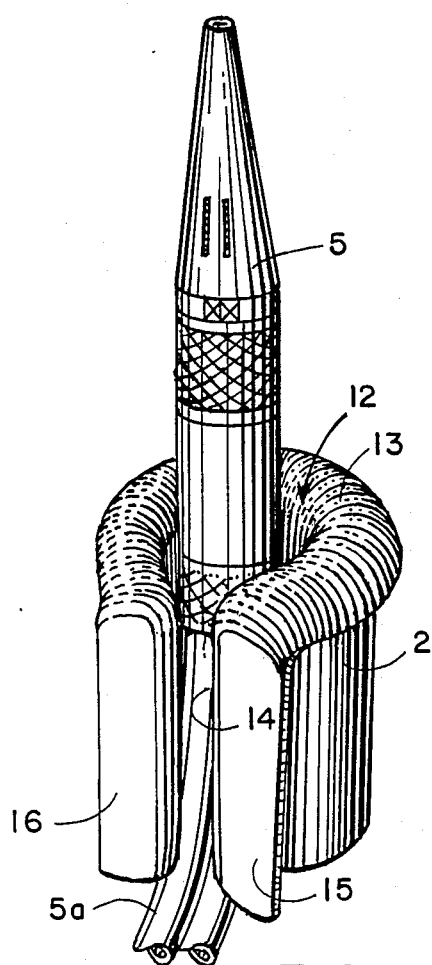
FIG. 14 is a front-elevational, perspective view showing the next preferred sequence of the application of the barrier in the hanger, specifically the insertion of the handpiece in the hanger while the barrier is in place.
Figure 15:
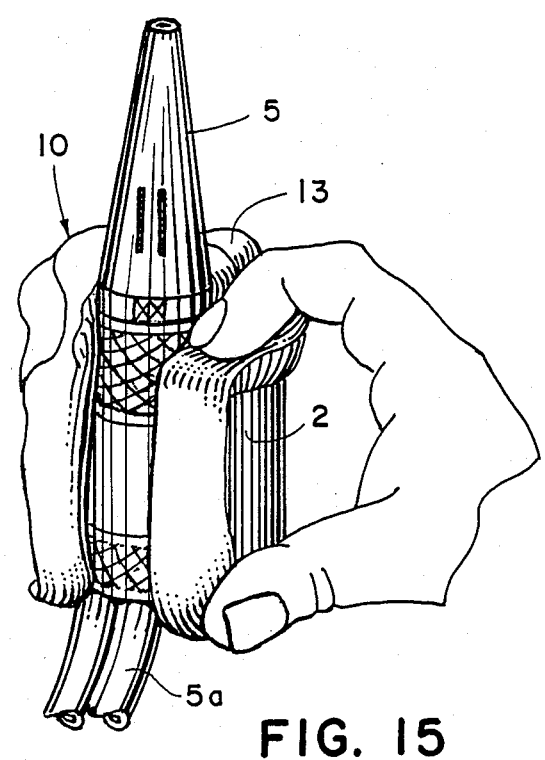
FIG. 15 is a front-elevational, perspective view of the barrier in place in a hanger with the handpiece firmly placed therein and illustrating the next sequence of application, specifically the adaptation of the barrier to the hanger by finger pressure on the barrier material causing it to conform more exactly to the shape of the hanger.

Referring now to FIGS. 13, 14 and 15, these figures disclose the sequence in mounting the barrier 10 in a hanger such as hanger 2 illustrated in FIG. 13. The back side 17 of the barrier 10 is grasped and the barrier is arranged above the hanger 2 as disclosed in FIG. 13. The barrier is then dropped into the central opening 2a of the hanger. As previously stated, the vertical or upright sleeve 11 of the barrier 10 is tapered so that it will easily fit into the opening 2a. The barrier drops into the opening 2a causing the apron 13 to rest on the top surface 19 of hanger 2 with the slot or vertical opening 14 of the barrier aligned with the slot or opening 20 of the hanger.

When placed within the hanger, the barrier covers all of the inside surfaces of the hanger, the top surface 19 of the hanger and the front surfaces 21 on each side of the slot 20, all as illustrated in FIG. 15. The next step is to insert the instrument inside the opening 1 of the barrier. This can be accomplished by the slot 14 receiving the leads 5a and then the instrument being dropped or forced downwardly (FIG. 14) until reaching the position as shown in FIG. 14. It should be understood that the barrier is deformable and, thus, the barrier's inside surface deforms to conform to the shape of the instrument.

After the instrument has been forced downwardly into the barrier, the top apron 13 is deformed around the top surface 19 of the hanger 2 and the front surfaces are deformed around both sides and bottom of the slot 21, so as to conform as nearly as possible with the shape of the hanger thus helping to retain the barrier in the hanger during the removal and replacement of the instrument in the barrier. This deforming of the barrier is illustrated by FIG. 14. It should be understood that the aluminum foil and the aluminum foil/plastic film laminate both have substantially no memory so that when deformed they will retain the deformed shape to aid in the barrier being retained in the hanger 2.

MODIFICATION

Figure 11:
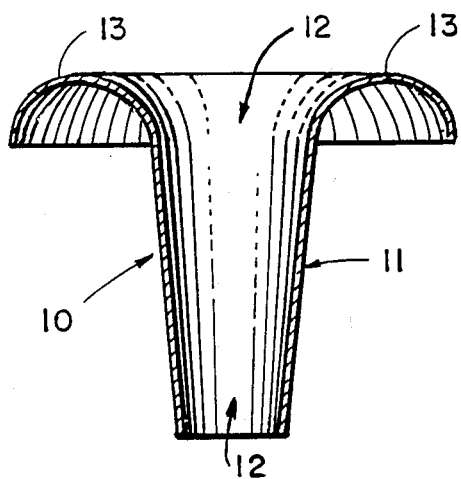
FIG. 11 is a front-elevational, cross-sectional view of the barrier of FIGS. 2-10 taken along the plane XI—XI of FIG. 3.
Figure 11A:
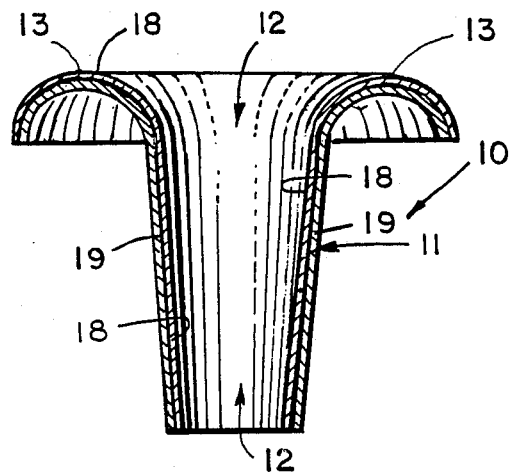
FIG. 11A is a front-elevational, cross-sectional view like FIG. 11 of a modified barrier in which the material from which the barrier is made is a laminate made up of aluminum foil and a plastic film.

As previously stated, one modification of the barrier is to construct it from an aluminum foil/plastic film laminate as disclosed in FIG. 11A. Another modification is to use this aluminum foil/plastic film laminate and cut out a rectangular portion or window 21 from the aluminum exposing the thin, flexible, translucent, plastic film 22 as disclosed in FIG. 16. This film has two important functions. One is that it is more flexible than the aluminum foil and in the type of hanger as identified by reference numeral 2 in FIG. 1, it allows the levers 9 of the automatic handpiece selector switches to be actuated during removal and replacement of handpieces in the hangers. Secondly, being translucent, the plastic film will permit transmission of a light beam such as that identified by reference numeral 23 in FIG. 18 that actuates a photoelectric switch in such type of handpiece selector hangers. When the embodiment with the plastic film window is used, the aluminum foil around the periphery of the sleeve 11 is still sufficiently rigid and is located in the proper position in the hanger so that the barrier will remain well-adapted to the hanger during removal and replacement of the handpiece.

Another modification of this invention is disclosed in FIG. 23, wherein rather than using a single laminate of aluminum foil and plastic film, two layers of plastic film are bonded to the aluminum foil—a front layer 25 and a back layer 26. This construction prevents possible separation of the plastic film and aluminum foil around the periphery of the window 21a as in FIGS. 16 and 23. In this case, each sheet of plastic film would be only approximately 0.0005" thick. This construction will produce substantially the same function as the laminated embodiment of FIGS. 16–22 and 24.

OPERATION

Having described the details of my invention and the three embodiments thereof, it should be evident that the barrier 10 is very easy to store, use and sterilize. The barrier 10 is constructed in a mold which forms the deformable material, which can be the aluminum foil only or the aluminum foil/thin plastic laminate, around a mold or die. When a window is to be utilized, the barrier can be formed of two separately formed pieces with the aluminum piece having the window cut out of it (FIG. 23) in which event the two pieces are adhered together in any well-known way such as an adhesive. On the other hand, the window can be cut out of the laminate (FIGS. 16–22 and 24) either after or before the barrier is formed.

Figure 12:
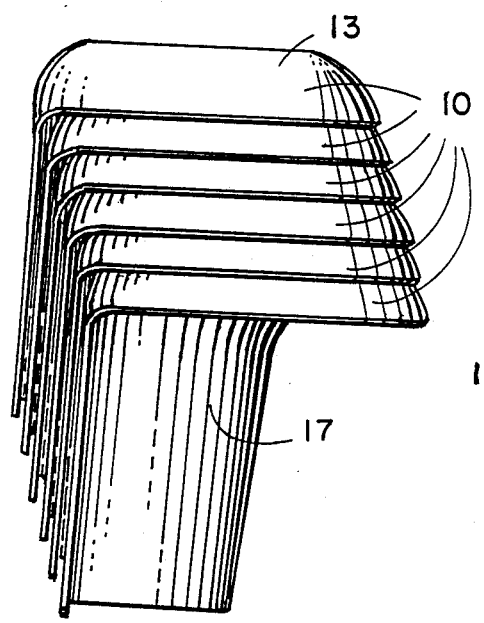
FIG. 12 is a side-elevational view of a stack of the barriers as disclosed in FIGS. 2-11.

The barriers are stacked together for packaging or storing as disclosed in FIG. 12. Each barrier is removed separately from the pack by grasping the back 17 of the sleeve 11 and then inserting the sleeve into the opening 2a of the hanger (see FIG. 13). Then the instrument is inserted into the barrier (FIG. 14) while it is in the hanger and the barrier is caused to be formed about the hanger (FIG. 15) so as to more nearly conform to the shape of the hanger to retain the barrier on the hanger as the instrument is removed or replaced.

It is evident that I have provided a preformed, disposable, sanitary barrier that is inexpensive, can easily be installed without contaminating the hands of the operator or the equipment, can be sterilized, stays in place while removing and replacing the handpiece from the hanger, and can be quickly removed and replaced by another after treatment is completed.

Having described my invention, it should be evident that although I have disclosed preferred forms, other forms and modification and embodiments can be utilized without departing from the spirit of this invention and it should be limited only as set forth within the following claims.

The embodiments of the invention in which an exclusive property or privilege is claimed are defined as follows:

1. A device for covering a dental or medical handpiece hanger for the purpose of preventing the contamination of such hanger such hanger having an opening to receive said instrument and inner and outer surfaces normally contacted by and for supporting said instrument comprising a shell constructed of a thin, deformable material molded to a shape to be received in the said opening of said hanger and to cover said inner support surfaces and at least portions of said outer surface, said deformable material having substantially no memory whereby when said shell is inserted in said hanger, it can be deformed and adapted to the said inner and outer surfaces so as to stay in place during removal and replacement of a handpiece.

2. The device of claim 1 in which a thin, tough, flexible, plastic film is bonded to the deformable material in a laminated construction to provide increased resistance to perforation and tearing during the placement and replacement of handpieces in said hanger, while maintaining the deformable, moldable properties of the aluminum foil.

3. The device of claim 2 in which a portion of the deformable material is removed from the center of the inside of the molded shell providing an opening which exposes the thin, flexible, plastic film in the area of said opening; whereby the free movement of levers or buttons attached to micro-switches or air valves, is permitted to activate or deactivate the power to the handpiece when it is removed or replaced into its hanger.

4. The device of claim 2 in which a portion of the deformable material is removed from the center of the inside of the molded shell providing an opening which exposes the thin, flexible, plastic film in the area of said opening; said plastic film being transparent whereby the transmission of a light beam which will activate a photo-electric switch is permitted to activate the power to the handpiece when it is removed from the hanger and to deactivate the power when the handpiece is replaced into the hanger.

5. The device of claim 2 in which the deformable material is aluminum foil.

6. The device of claim 3 in which the deformable material is aluminum foil.

7. The device of claim 4 in which the deformable material is aluminum foil.

8. The device of claim 2 in which the plastic film is polyethylene.

9. The device of claim 3 in which the plastic film is polyethylene.

10. The device of claim 4 in which the plastic film is polyethylene.

11. A device for covering a dental or medical handpiece hanger for the purpose of preventing the contamination of such hanger; said hanger comprising a generally hollow cylinder with an opening for receiving said instrument extending axially through said cylinder whereby said cylinder has inner and outer wall surfaces; a longitudinal slot in the wall of said cylinder; said shell having a tapered quasi-cylindrical shape, the diameters of said shell being of a size whereby said shell fits into said opening, said diameters being progressively less from top to bottom so as to facilitate insertion of said shell in the opening of said hanger, said shell also having a longitudinal slot located so as to be aligned with the slot in said hanger; flanges located along the top of said shell and along the edges of said longitudinal slot of said shell for covering any exposed areas of said hangers which might be contacted by said instrument.

12. The device of claim 11 in which the shell is molded from a deformable material having no memory whereby when said shell is inserted in said hanger, it can be deformed and adapted to the said inner and outer surfaces so as to stay in place during removal and replacement of a handpiece.

13. The device of claim 11 in which a portion of said shell is transparent whereby the transmission of a light beam which will activate a photo-electric switch is permitted to activate the power to the handpiece when it is removed from the hanger and to deactivate the power when the handpiece is replaced into the hanger.

14. The device of claim 12 in which a thin, tough, flexible plastic film is bonded to the deformable material in a laminated construction to provide increased resistance to perforation and tearing during the placement and replacement of handpieces in said hanger while maintaining the deformable, moldable properties of the aluminum foil.

15. The device of claim 14 in which a portion of the deformable material is removed from the center of the inside of the molded shell providing an opening which exposes the thin, flexible plastic film in the area of said opening; whereby the free movement of levers or buttons attached to micro-switches or air valves is permitted to activate or deactivate the power to the handpiece when it is removed or replaced into its hanger.

16. The device of claim 11 in which the shell is thin aluminum foil.

17. The device of claim 12 in which the shell is thin aluminum foil.

18. The device of claim 13 in which the shell is thin aluminum foil.

19. The device of claim 14 in which the shell is thin aluminum foil.

* * * * *